United States Patent [19]

Brush et al.

[11] 4,165,372

[45] Aug. 21, 1979

[54] 6-CARBOXY-1-PHENYL-2,3,4,5-TETRAHYDRO-1H-3-BENZAZEPINE COMPOUNDS AND USE AS DOPAMINERGIC AGENTS

[75] Inventors: Charles K. Brush, Malvern; Joseph Weinstock, Phoenixville, both of Pa.

[73] Assignee: SmithKline Corporation, Philadelphia, Pa.

[21] Appl. No.: 852,404

[22] Filed: Nov. 17, 1977

[51] Int. Cl.² ............... A61K 31/55; C07D 233/16
[52] U.S. Cl. ............... 424/244; 260/239 BB; 260/340.7
[58] Field of Search ............... 260/239 BB, 340.7; 424/244

[56] References Cited

U.S. PATENT DOCUMENTS 3,393,192   7/1968   Walter et al. ............... 260/239 BB

*Primary Examiner*—Donald G. Daus
*Assistant Examiner*—D. B. Springer
*Attorney, Agent, or Firm*—William H. Edgerton

[57] ABSTRACT

A group of 1-phenyl-3-benzazepines with structures characterized by having a carboxy derived substituent at position 6 which are dopaminergic agents or are intermediates for preparing other dopaminergic agents. Particular illustrative species include 6-carbomethoxy-7,8-dihydroxy-3-methyl-1-phenyl-2,3,4,5-tetrahydro-1H-3-benzazepine, 6-carboxy-7,8-dihydroxy-1-phenyl-2,3,4,5-tetrahydro-1H-3-benzazepine and 6-carbomethoxy-7,8-dihydroxy-1-(4'-hydroxyphenyl)-2,3,4,5-tetrahydro-1H-3-benzazepine.

15 Claims, No Drawings

6-CARBOXY-1-PHENYL-2,3,4,5-TETRAHYDRO-1H-3-BENZAZEPINE COMPOUNDS AND USE AS DOPAMINERGIC AGENTS

This invention comprises a new group of compounds which are 1-phenyl-2,3,4,5-tetrahydro-1H-3-benzazepines having at least three substituents in the benz-ring of the nucleus, one of which is a carboxy derived group substituted at the 6-position. These compounds have utility as dopaminergic compounds active at peripheral and/or at central dopaminergic centers. They therefore, for example, either demonstrate activity in animal tests which are known to predict anti-Parkinsonism activity by means of the activity at central dopamine receptors or in animal tests which measure cardiovascular effects resulting from activity at peripheral receptors. Even more important they are useful intermediates for preparing other 1-phenyltetrahydrobenzazepines which have more pronounced dopaminergic activity such as the 6-lower alkyl congeners.

The structures of the compounds of this invention are specifically identified by having a carboxy or a carboxy derived substituent such as a —$CO_2H$, —$CO_2$alk, —COalk, —$CONH_2$ or —CHO group at the 6-position of the 1-phenyltetrahydro-3-benzazepine system. Exemplary of this new group of compounds are those represented by the following structural formulas:

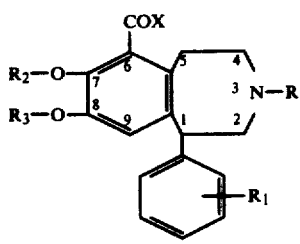

in which:
R is hydrogen, benzyl, phenethyl, lower alkanoyl of from 1–5 carbons such as formyl, acetyl or trifluoroacetyl, lower alkyl of 1–5 carbon atoms especially methyl, hydroxyethyl, lower alkenyl of 3–5 carbon atoms such as allyl or dimethylallyl, propargyl, furylmethyl, thienylmethyl or phenacyl;
$R_1$ is hydrogen or one or two substituents such as trifluoromethyl, halo such as chloro, bromo or fluoro, methyl, methoxy, acetoxy, methylthio or especially hydroxy;
$R_2$ and $R_3$ are each hydrogen, lower alkyl of 1–5 carbon atoms especially methyl, lower alkanoyl of 2–5 carbon atoms especially acetyl, benzyl or, when taken together, methylene; and
X is hydroxy, hydrogen, amino, lower alkyl of 1–5 carbon atoms, lower alkoxy of 1–5 carbon atoms or, when R, $R_1$, $R_2$ or $R_3$ are chemically inert thereto, chloro or bromo;
$R_2$ and $R_3$ are preferably hydrogen for maximal biological activity. For intermediate use, $R_2$ and $R_3$ are preferably methyl or benzyl. Prime blocking groups at 3 are trifluoroacetyl and formyl.

A subgeneric group of compounds within the above illustrative generic group are those of Formula I in which:
R is hydrogen or methyl;
$R_1$ is H or hydroxy preferably in the para position;
$R_2$ and $R_3$ are the same and are hydrogen, methyl or acetyl; and
—COX is carbomethoxy, carboethoxy or carboxy.

Individual compounds of note are those of Formula II:

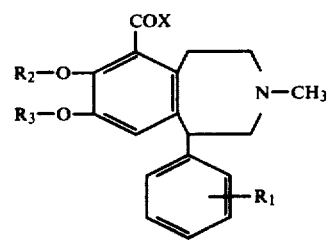

in which:
$R_1$ is hydrogen or p-hydroxy;
$R_2$ and $R_3$ are the same and are hydrogen; and
X is methoxy or hydroxy.

The compounds in which the 7,8-dihydroxy groups are etherified such as the methoxy, benzyloxy or methylenedioxy-containing compounds as well as the compounds having a 6-acid chloride, 6-amido, 6-formyl and 6-carboxy group are of primary interest as intermediates. The 6-carbomethoxy and 6-carboethoxy compounds are active dopaminergic compounds especially with a 3-methyl or a 1-(4'-hydroxyphenyl) substituent.

The addition salts which are acceptable as nontoxic for pharmaceutical purposes or in general for synthetic purposes but which have the utility of the corresponding free bases of Formula I are included in this invention. These salts are prepared by methods well known to the art and may be formed with both inorganic or organic acids, for example: maleic, fumaric, benzoic, ascorbic, pamoic, succinic, bismethylenesalicyclic, methanesulfonic, ethanedisulfonic, acetic, oxalic, propionic, tartaric, salicyclic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. Similarly the quarternary salts include those prepared from organic halides such as methyl iodide, ethyl iodide, benzyl chloride and the like as known to the art. When a carboxy group is present at position 6, carboxylic salts derived from strong bases are possible, for example, those having cations such as potassium, sodium, lithium, ammonium, calcium and the like.

It will be obvious to one skilled in the art that the compounds of Formula I may be present as diastereoisomers which may be revolved into d, l optical isomers. Resolution of the optical isomers may be conveniently accomplished by fractional crystallization of their salts with optically active acids from appropriate solvents. Unless otherwise specified herein or in the claims, it is intended to include all isomers, whether separated or mixtures thereof. Where isomers are separated, the desired pharmacological activity will usually predominate in one of the isomers.

PRIOR ART STATEMENT

Certain 1-phenyl-2,3,4,5-tetrahydro-1H-3-benzazepines have been described in U.S. Pat. Nos. 3,393,192 and 4,011,319; British Pat. No. 1,118,688; and Swiss Pat. No. 555,831, including general methods of preparation of the 1-phenyl-2,3,4,5-tetrahydro-1H-3-benzazepine ring system. However these references disclose no 6-carboxy derived substitution in the structures.

In an earlier filed still pending application, U.S. Ser. No. 742,695 filed Nov. 17, 1976, the preparation of 6-bromo-7,8-dimethoxy-1-phenyl-2,3,4,5-tetrahydro-1H-3-benzazepine by direct bromination at the 6-position was described along with the use of the compound as an intermediate for preparing the 6-lithium compound. The 6-bromo and 6-lithium products are the most convenient starting materials for preparing the compounds of the present invention.

One skilled in the art will recognize that the 6-lithium intermediates form a 6-carbanion. Any 6-metal congener which likewise will form such a carbanion will also be useful in forming the 6-carboxy derived compounds of Formula I such as the Grignard reagent (6-MgBr) or various aluminum or copper complexes as known to the art.

The compounds of this invention are prepared by reacting the 6-lithium intermediates with carbon dioxide to form the 6-carboxy-1-phenyl-2,3,4,5-tetrahydro-1H-3-benzazepines of Formula I or with a formylating agent such as N-methylformanilide or another tertiary formamide to prepare the 6-formyl-1-phenyl-2,3,4,5-tetrahydro-1H-3-benzazepines of Formula I. Any chemical centers of the structures which may be reactive under the conditions for forming a 6-metal benzazepine and reacting it with carbon dioxide or a formylating agent should be protected such as by forming the ether or ester derivatives of hydroxy substituents or, at reactive hydrogen centers such as at 3, by salt or acyl formation. Referral to the preparation and reactions of lower alkyl lithium reagents may be had to *The Chemistry of Organic Lithium Compounds*, Wakefield, Pergamon (1976).

The reaction is most conveniently run in the cold such as at about −80° to 0° C. in an inert solvent in which the reactants are soluble such as ethyl ether, pentane, tetrahydrofuran, toluene and such or solvent mixtures thereof. Molar equivalents of the carbanion producing reagent and the carboxylating reagent may be used but an excess of the latter is most convenient. The reaction proceeds readily and is usually complete within 1–6 hours. It is also often convenient not to isolate the 6-lithium intermediate prepared as previously described.

In some cases the most advantageous N-substituent is hydrogen which requires an extra equivalent of the alkyl lithium reagent. In other cases the most advantageous N-substituents are the formyl or trifluoroacetyl groups. These react with an equivalent of the alkyl lithium to form hemiaminal derivatives which are hydrolyzed by acid as part of the workup procedure to give the secondary amine products, i.e.

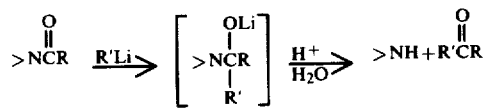

The methyl ester of the carboxylic acid substituent at 6 is prepared by normal Fischer acid catalyzed esterification. However, due to the extreme steric hindrance higher esters are best prepared by reaction of the acid with a strong acid in strongly acidic media to give the aroyl carbonium ion,

which is then reacted with the appropriate alcohol. An alternative route is by preparing the metal (potassium or sodium is preferred) salt of the acid and reacting this with a lower alkyl halide.

The compounds of Formula I in which X is lower alkyl, i.e. the 6-acyl compounds, are produced by reacting the 6-carbalkoxy compounds, produced as above and protected, if necessary, at the 3, 7 and 8 positions, with a lower alkyl lithium. These 6-acyl derivatives are used as intermediates for preparing the corresponding 6-lower alkyl and 6-α-hydroxy-lower alkyl-1-phenyl-2,3,4,5-tetrahydro-1H-3-benzazepines which have dopaminergic activity. Reduction of the 6-lower alkanoyl compounds with a keto reducing agent such as sodium borohydride-isopropanol or, alternatively and preferably, reaction of the 6-aldehyde with an alkyl lithium compound gives the 6-α-hydroxy compound which in turn may be converted into 6-lower alkyl-7,8-dihydroxy-1-phenyl-2,3,4,5-tetrahydro-1H-3-benzazepines.

The compounds of Formula I in which X is chloro, bromo, amino, monoalkylamino or dialkylamino are prepared by reacting the compounds of Formula I having a 6-carboxy group protected at positions 3, 7 and 8 by such groups as 3-acyl or 7 and 8 ethers with thionyl chloride or bromide to form the intermediate 6-acyl halide which is then reacted with ammonia or a lower alkyl amine to produce 6-carbamyl-1-phenyl-2,3,4,5-tetrahydro-1H-3-benzazepines and the N-mono- and di-lower alkyl derivatives thereof of Formula I. These are intermediates for preparing 6-amino or 6-aminomethyl-7,8-dihydroxy-1-phenyl-2,3,4,5-tetrahydro-1H-3-benzazepines having potential dopaminergic activity by methods known to the art.

As stated above the 6-bromo starting materials for the preparation of the compounds of this invention are most conveniently prepared by direct 6-bromination of a suitably protected and substituted 1-phenyl-2,3,4,5-tetrahydro-1H-3-benzazepine. If this reaction is not applicable the compounds may be prepared by the cyclization in the presence of sulfuric acid, polyphosphoric acid or a similar carbonium ion generating agent of a compound of the formula:

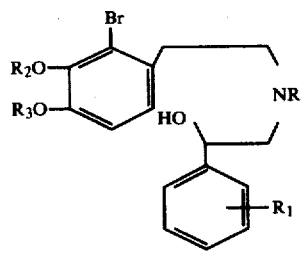

in which R–R$_3$ are as defined above being either protected or substituted by groups inert under the reaction conditions.

Mixed alkoxy substituted compounds are prepared by selecting the proper phenethylamine starting material for preparing Formula III. To obtain the 6-bromobenzazepine products wherein R$_2$ and R$_3$ are hydrogen, cyclization of the corresponding methoxy substituted intermediates may be carried out with 48% hydrobromic acid at reflux temperature for from two to four hours whereby simultaneous demethylation of the methoxy groups occurs. Alternatively they may be split later by reaction of the compound of Structure I with boron tribromide.

To prepare the compounds of Formula I where R is hydroxyethyl, lower alkyl or alkenyl, phenacyl, propargyl, phenethyl, benzyl, etc., the corresponding benzazepines wherein R is hydrogen may be alkylated by standard methods with ethylene oxide, a reactive lower alkyl halide such as the bromide or chloride, a reactive alkenyl halide such as an allyl bromide or chloride or, in certain cases as known to the art, by N-acylation followed by amide reduction. The latter is used to prepare 3-furylmethyl and thienylmethyl derivatives. Advantageously, to obtain the products where $R_2$ and/or $R_3$ are hydrogen the reaction with the alkylating agent is carried out on the corresponding methoxy substituted benzazepines in an inert solvent such as methanol or acetone, preferably at reflux temperature and in the presence of a basic condensing agent such as potassium hydroxide or carbonate. Treatment of the resulting product as stated above with, for example boron tribromide or other ether splitting agents gives the active hydroxy substituted benzazepines.

The important compounds of Formula I where R is methyl are conveniently prepared from methoxy substituted benzazepines wherein R is hydrogen by a reductive formylation reaction with formic acid/formaldehyde. Treatment of the resulting product with boron tribromide gives once again the corresponding 7,8-dihydroxy substituted benzazepines.

To prepare the compounds of Formula I in which $R_2$ or $R_3$ is alkanoyl whenever there are no interfering substituents, the corresponding 3-benzyl-7,8-dihydroxy-3-benzazepine (obtained by N-alkylation of the hydroxybenzazepine with benzyl bromide in the presence of potassium carbonate) is treated with the appropriate alkanoic acid anhydride or chloride, for example acetic anhydride, and the resulting alkanoyloxy substituted benzazepine is then hydrogenated in the presence of palladium-on-carbon to remove the protective benzyl group. The dialkanoyloxy derivatives such as the important 7,8-diacetoxy compounds can also be prepared by direct O-acylation of the 6-carboalkoxy-7,8-dihydroxy-1-phenyl-2,3,4,5-tetrahydro-1H-3-benzazepine hydrobromide in trifluoroacetic acid at ambient temperature with the anhydride or halide. The N or 3-lower alkanoyl congeners in the dihydroxy series may be prepared conveniently by N-acylating the methylenedioxy derivative followed by splitting the protective group. Also direct N-alkanoylation of the dihydroxy compounds is possible under controlled conditions and quantities of reactants as known to the art. As noted in the illustrative examples any undesirable O-acylation may necessitate a mild hydrolysis treatment.

The intermediates of Formula III above are conveniently prepared by heating equimolar amounts of a styrene oxide with a 3,4-dialkoxyphenethylamine which is either known or prepared by methods known to the art, each appropriately substituted, either alone or in an inert organic solvent such as tetrahydrofuran. Preferably the heating is effected on a steam bath or at reflux temperature for from 12 to 24 hours. The required styrene oxide is conveniently prepared by reaction of the ylide derivative from sodium hydride and trimethylsulfonium iodide with the appropriately substituted benzaldehyde.

Another useful preparation of the intermediate compounds of Formula III includes reaction of the appropriate mandelic ester to form a mandelamide and reducing this with diborane to obtain the required intermediate. Still another preparation involves the reaction of the appropriate phenethylamine with an appropriate bromohydrin ether to give a protected ether of III which is then deprotected.

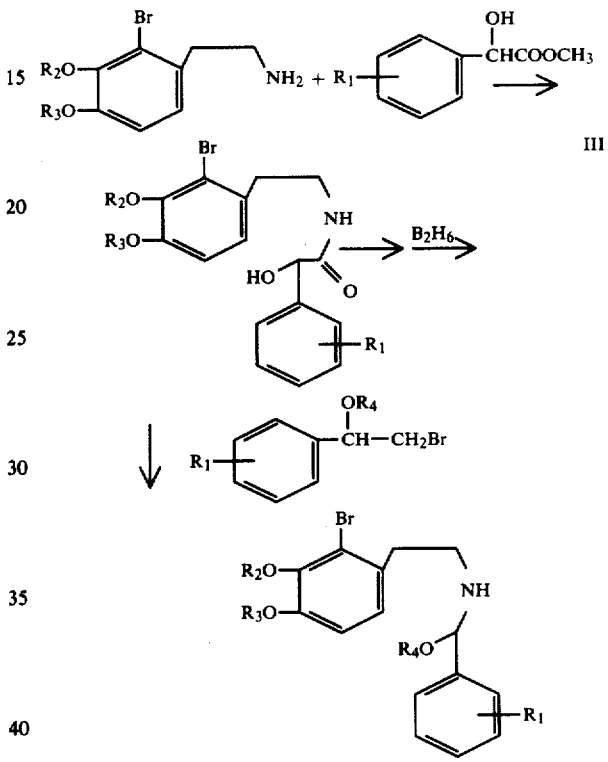

III in which $R_4$=tert.-butyl- or tetrahydropyranyl-.

The benzazepine compounds of Formula I especially those in which X is alkoxy have antiparkinsonism activity due to central dopaminergic activity as demonstrated by employing a modified standard animal pharmacological test procedure reported by Ungerstedt et al., in Brain Research 24, 1970, 485-493. The activity in the compounds of Formula I which have biological activity may in certain cases be more pronounced than the peripheral or cardiovascular activity. This test procedure is based on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rat turning model. These compounds directly activate the dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value. For example 6-carbomethoxy-7,8-dihydroxy-1-phenyl-2,3,4,5-tetrahydro-1H-3-benzazepine hydrochloride had an $RD_{500}$ (i.p.) of 0.3 mg/kg. The 6-carboxy had an $RD_{500}$ (i.p.) of 4.5 mg/kg as the hydrobromide. 6-Carbomethoxy-7,8-dihydroxy-3-methyl-1-phenyl-2,3,4,5-tetrahydro-1H-3-benzazepine hydrochloride had an $RD_{500}=0.22$ mg/kg (i.p.); at 6 mg/kg (p.o.) had 486±257 turns (4 hours) and at 10 mg/kg (p.o.) had 323±137 turns (4 hours). It demonstrated no renal vasodilator activity at from 3-300 µg/kg. 6-Carboxy-7,8-dihydroxy-3-methyl-1-phenyl-2,3,4,5-tetrahydro-1H-3-benzazepine hydrobromide i.p. had an $RD_{500}$ of 0.03 mg/kg; (p.o.) at 6 mg/kg, 411±239 turns (4 hours) and at 10 mg/kg (p.o.), 826±239 turns (4 hours). In general the longer chain carboalkoxy congeners were of lower activity.

The peripheral or cardiovascular dopaminergic activity of the compounds of this invention is demonstrated using the methods of testing described in the previous application referred to as well as in U.S. Pat. No. 3,011,319. For example 6-carbomethoxy-7,8-dihydroxy-1-phenyl-2,3,4,5-tetrahydro-1H-3-benzazepine hydrochloride at 20 mg/kg (p.o.) increased phase IV renal plasma flow and potassium excretion in the mannitol renal clearance test in dogs. The same compound had an $ED_{15}$ (i.v.) of 260 µg/kg in the anesthetized dog compared to dopamine's 2.7 µg/kg value in decreasing renal vascular resistance. 6-Carbomethoxy-7,8-dihydroxy-1-(4'-hydroxyphenyl)-2,3,4,5-tetrahydro-1H-3-benzazepine hydrochloride was active in the preliminary cardiovascular screen for renal vasodilator activity in the dog at 30 µg/kg/min. While the compounds of this invention noted above to be used primarily as intermediates have dopaminergic activity, some of them have undesirable biological properties such as the 6-formyl or carbamyl.

The pharmaceutical compositions of this invention containing a compound of Formula I which has dopaminergic activity are prepared in conventional dosage unit forms by incorporating the chemical compound or a pharmaceutically acceptable acid addition salt thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 150 mg to about 1000 mg of active ingredient per dosage unit but this quantity depends on the specific biological activity desired and the condition of patient.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier for oral administration is used the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses will be administered several times such as two or three times a day with the daily dosage regimen being selected from about 300 mg to about 2 g. When the method described above is carried out antiparkinsonism or hypotensive activity is produced with a minimum of side effects. The terms "lower alkyl", "lower alkoxy", "lower alkanoyl" and such alone or combined are used to mean chemically stable straight or branched aliphatic groups having up to 5 carbon atoms.

The following examples are designed solely to illustrate the preparation and use of the compounds of this invention. The temperatures are Centigrade. Other variations of these examples will be obvious to those skilled in the art.

PREPARATION A 7,8-Dimethoxy-1-phenyl-2,3,4,5-tetrahydro-1H-3-benzazepine (280 g, 0.75 mole) was dissolved in 1700 ml of acetic acid. Bromine (280 g, 1.75 mole) was added in a thin stream. The reaction was stirred for two hours. The precipitate, which formed after 1 hour, was collected and washed with ether. It was dissolved in boiling methanol and acetone was added to destroy the bromine excess. 6-Bromo-7,8-dimethoxy-1-phenyl-2,3,4,5-tetrahydro-1H-3-benzazepine hydrobromide was allowed to crystallize from the methanol and a second crop was obtained by adding ether to the mother liquor. Yield 298 g, 77% m.p. 236°-238°. This bromination may be applied to any 7,8-dialkoxy or alkanoyloxybenzazepine having a free 6-position in which the substituted 1-phenyl ring is not more reactive to halogenation than is the 6-position of the nucleus.

PREPARATION B

Dry dimethylformamide (500 ml) was deoxygenated four times by pulling a vaccum and refilling the evacuated flask with argon. 7,8-Dihydroxy-1-phenyl-3-trifluoroacetyl-2,3,4,5-tetrahydro-1H-3-benzazepine (53.4 g, 0.152 mole) was added and dissolved as the solution and flask were deoxygenated once more. Methylene bromine (52.5 g, 0.3 mole), potassium carbonate (50 g, 0.36 mole) and cupric oxide (1.3 g) were added and the solution was deoxygenated a final time. The reaction was heated at 150° under argon for 2 hours.

It was worked up by pouring into 2 l. of ice water while stirring. The aqueous suspension was extracted 4 times with 300-400 ml ether, and the ether was back extracted 3 times with 1.5 l. water. The ether was dried and evaporated. The residue was dissolved in chloroform and chromatographed over silica gel. The yield of 7,8-methylenedioxy-1-phenyl-3-trifluoroacetyl-2,3,4,5-tetrahydro-1H-3-benzazepine was 35.3 g (64%); m.p. 94°-96° from cyclohexane.

This compound (31.8 g, 0.0876 mole) was dissolved in 105 ml of acetic acid and bromine (4.86 cc, 0.089 mole) was added all at once. The reaction stirred at room temperature overnight. The flask was then cooled and the solid was collected. The mother liquors were warmed, diluted with water and then allowed to cool. A second crop was collected. To the mother liquor was added a small amount more of bromine. It stirred for two days at room temperature and the relatively small amount of precipitate was collected. The crude material was recrystallized from acetic acid to give 28 g (72%) of the 6-bromo compound, m.p. 160°-165°.

The 6-bromo compound (28 g) was suspended in 250 ml of methanol, 50 ml of 40% sodium hydroxide was added and the reaction mixture was heated to boiling. The mixture was then stirred for one hour. The methanol was stripped off and water and ether were added to the residue. The layers were shaken, separated and the water was washed again with ether. The ether layers were dried and ethereal hydrogen chloride was added. The precipitate was recrystallized from methanol-ethyl acetate to give 6-bromo-7,8-methylenedioxy-1-phenyl-2,3,4,5-tetrahydro-1H-3-benzazepine hydrochloride, 21.3 g (88%), m.p. 240°-248°.

PREPARATION C

A mixture of 4.9 g of 6-bromo-7,8-dimethoxy-1-phenyl-2,3,4,5-tetrahydro-1H-3-benzazepine, 0.02 ml of n-butyl bromide and 0.02 mol of potassium hydroxide is dissolved in 120 ml of dry methanol and refluxed for 48 hours. The reaction mixture is evaporated to dryness, taken up in ethyl acetate and filtered to remove inorganic salts. The filtrate is washed with water, dried and evaporated to give 3-n-butyl-6-bromo-7,8-dimethoxy-1-phenyl-2,3,4,5-tetrahydro-1H-3-benzazepine.

The 3-n-butylbenzazepine (0.01 mol) is dissolved in 120 ml of dry methylene chloride and 0.032 mole of boron tribromide is added dropwise at −10° C. The solution is warmed to room temperature and stirred for two hours. The excess boron tribromide is destroyed with methanol added dropwise with ice-cooling. The cold solution is refluxed on the steam bath to remove hydrogen bromide and trimethyl borate and then evaporated to yield 3-n-butyl-6-bromo-7,8-dihydroxy-1-phenyl-2,3,4,5-tetrahydro-1H-3-benzazepine hydrobromide.

PREPARATION D

In a dry flask containing 10 mmole of piperonal cyclohexylimine was placed 75 ml of dry tetrahydrofuran. The mixture cooled to −78°, and 10.5 mmol of butyl lithium in hexane was added over a 5 minute period. This was stirred for 15 minutes at −78°, and then a solution of 15 mmol of hexachloroethane in dry tetrahydrofuran added dropwise. This was stirred for 15 minutes, warmed to room temperature, and poured into water. This was extracted with methylene chloride, which was evaporated under vacuum and hydrolyzed by 10% aqueous hydrochloric acid to give 2-bromopiperonal. Reference: F. E. Ziegler and K. W. Fowler, J.O.C. 41 1564 (1976). This product is reduced with sodium borohydride, reacted with sodium cyanide and the resulting phenyl-acetonitrile reduced with borane to give the phenethylamine. This compound is condensed with p-methoxystyrene oxide to give the α-hydroxyphenethylamine intermediate which is reacted with an excess of trifluoroacetic acid at room temperature for 18 hours to give 6-bromo-7,8-methylenedioxy-1-p-methoxyphenyl-2,3,4,5-tetrahydro-1H-3-benzazepine. This compound is optionally split using boron trichloride to give 6-bromo-7,8-dihydroxy-1-p-methoxyphenyl-2,3,4,5-tetrahydro-1H-3-benzazepine or with borontribromide to give 6-bromo-7,8-dihydroxy-1-(p-hydroxyphenyl)-2,3,4,5-tetrahydro-1H-3-benzazepine.

PREPARATION E

Isovanillin (76.1 g, 0.5 m) was suspended in 750 ml of chloroform. Bromine (27.3 ml, 0.5 m) in 200 ml of chloroform was added at 0° slowly. Water was added to give the desired 2-bromo-3-hydroxy-4-methoxybenzaldehyde, m.p. 197°-203°.

The aldehyde product (46.2 g, 0.2 mole) was dissolved in 300 ml of dry dimethylformamide, 69.1 g of potassium carbonate was added. 28.4 ml (0.30 mole) of dimethylsulfate was added at room temperature dropwise. After the addition the reaction was heated on the steam bath for 10 minutes. 29 ml of water was added dropwise and the reaction again heated for 5 minutes on the steam bath. The reaction was then poured into ice water and the precipitate collected, 2-bromo-3,4-dimethoxybenzaldehyde, m.p. 80°-81.5°.

The dimethoxybenzaldehyde (10 g, 0.04 mole) was dissolved in 100 ml of ethanol 5 g (0.132 mole) of sodium borohydride was added. The reaction was stirred for 1 hour. The reaction mixture was poured into water and extracted into methylene chloride to give the benzyl alcohol (m.p. 74°-76.5°). This was converted to the benzyl chloride as a tan liquid, using benzene and conc. hydrochloric acid then to the benzyl cyanide, m.p. 48°-55° using sodium cyanide in dimethylsulfoxide.

The benzyl cyanide (8.05 g, 0.315 mole) was dissolved in 80 ml of dry tetrahydrofuran and then added slowly to 80 ml of 1 M boron trifluoride in tetrahydrofuran at 5°. After refluxing for 2 hours, the mixture was cooled and 40 ml of methanol added carefully. After refluxing shortly and standing overnight the mixture was concentrated to give a tan oil. Dilute hydrochloric acid was added. The material was washed with ether, filtered and the filtrate made basic with 40% sodium hydroxide. After extracting with ether, washing, drying and evaporated the extracts the desired phenethylamine was obtained as a viscous, light yellow oil.

The phenethylamine (0.12 mole) is heated to 115° in an oil bath. Styrene oxide (14.4 g, 0.12 mole) is added and the reaction heated for 1 hour. After cooling to ~30°, 2:1 petroleum ether/acetone is added to give N-[(2-hydroxy-2-phenylethyl)]-N-[2-(2'-bromo-3',4'-dimethoxyphenyl)ethyl]amine.

The hydroxyphenethylamine (0.0445 mole) is dissolved in 60 ml of trifluoroacetic acid and 4.05 ml of concentrated sulfuric acid is added. The reaction is refluxed for 2 hours. After cooling most of the trifluoroacetic acid is stripped off and the residue is poured into water. It is made basic with 10% sodium hydroxide and extracted with ether twice. The ether is dried and evaporated to give 6-bromo-7,8-dimethoxy-1-phenyl-2,3,4,5-tetrahydro-1H-3-benzazepine. The dimethoxy derivative is converted to 6-bromo-7,8-dihydroxy-1-phenyl-2,3,4,5-tetrahydro-1H-3-benzazepine hydrobromide using boron tribromide.

Using this general procedure with variously substituted styrene oxides having one or more methyl, methoxy, methylthio, trifluoromethyl groups gives the corresponding 6-bromo intermediates for preparing the 6-carboxy derived compounds of this invention as described hereafter.

EXAMPLE 1

A mixture of 50 ml of a 1 M solution of n-butyl lithium in 150 ml of ethyl ether was cooled to −78° at which time a solution of 22.9 g (0.051 mole) of 6-bromo-3-benzyl-7,8-dimethoxy-1-phenyl-2,3,4,5-tetrahydro-1H-3-benzazepine (prepared by N-benzylation of the product of Preparation A using benzyl chloride) in 200 ml of ethyl ether was added over 15 minutes. After adding an excess of dry ice and being allowed to stir while the temperature rose to room temperature, the lithium salt of the 6-carboxy product was separated by filtration.

The salt was dissolved in 150 ml of water. The resulting mixture was extracted with ethyl ether. The aqueous solution was made acid with hydrochloric acid and the salt collected by filtration. The solid was slurried in benzene and stripped down. Ether was added and the salt was separated by filtration then dissolved in base. 10% Hydrochloric acid was added to pH 7.5. The precipitate was dried to give the desired 6-carboxy-3-benzyl-7,8-dimethoxy-1-phenyl-2,3,4,5-tetrahydro-1H-3-benzazepine, m.p. 145°–153°. A high melting form, m.p. 230°–232°, was obtained using boiling acetone. One of these may have the proton at the basic N-member of the nucleus, the other at the carboxy substituent at 6.

EXAMPLE 2

A mixture of 25 g (0.068 mole) of 6-bromo-7,8-dimethoxy-1-phenyl-2,3,4,5-tetrahydro-1H-3-benzazepine in a minimum amount of toluene diluted with ethyl ether under dry, degassed conditions was reacted with 100 ml (0.24 mole) of n-butyl lithium in 100 ml of ethyl ether at −78°.

After a few minutes, the mixture was poured onto a slurry of dry ice (carbon dioxide). The ether slurry was extracted with water. The aqueous extracts were extracted with ether, then acidified with dilute hydrochloric acid and warmed on the steam bath briefly. The acid layer was extracted with ether then stripped to leave a solid product, 6-carboxy-7,8-dimethoxy-1-phenyl-2,3,4,5-tetrahydro-1H-3-benzazepine hydrochloride, m.p. 225°–226° (dec.). More product, m.p. 230°–235°, was obtained from the mother liquor by the use of sodium bicarbonate, ethyl acetate extraction and acidification with hydrochloric acid.

EXAMPLE 3

A mixture of 8 g (0.022 mole) of 6-carboxy-7,8-dimethoxy-1-phenyl-2,3,4,5-tetrahydro-1H-3-benzazepine hydrochloride in 100 ml of dry benzene and 16 ml of trifluoroacetic anhydride was stirred then 16 ml of n-butanol was added dropwise while the mixture cooled to room temperature in a water bath. The solvents were stripped off to leave the N-trifluoroacetylbutyl ester.

This product was dissolved in 200 ml of methanol and 15 ml of 40% sodium hydroxide solution was added. After stirring for 3 hours at 25°, the methanol was stripped off. Aqueous ethyl ether was added. The ether layer was washed and dried. Ethereal hydrogen chloride was added to give the desired 6-carbobutoxy-7,8-dimethoxy-1-phenyl-2,3,4,5-tetrahydro-1H-3-benzazepine hydrochloride, m.p. 224°–228°.

EXAMPLE 4

The product from Examples 3 (5.7 g, 0.0136 mole) was dissolved in 500 ml of methylene chloride with 5.1 ml of boron tribromide at −15°. After 4 hours, 25 ml of conc. ammonium hydroxide was added with a small amount of ascorbic acid. The pH was taken to 8 with carbonate solution. The water layer was separated and extracted with ethyl acetate using sodium chloride to salt out the product which was collected and stirred with dilute hydrochloric acid overnight. The mixture was filtered. The filtrate was stripped until a solid formed. Cooling gave the desired 6-carbobutoxy-7,8-dihydroxy-1-phenyl-2,3,4,5-tetrahydro-1H-3-benzazepine hydrochloride, m.p. 217°–220° (dec.).

A similar procedure was used on the product of Example 2 to give 6-carboxy-7,8-dihydroxy-1-phenyl-2,3,4,5-tetrahydro-1H-3-benzazepine hydrobromide hydrate, m.p. 220°–222° (dec.)

EXAMPLE 5

A mixture of 3.0 g (0.0079 mole) of 6-carboxy-7,8-dihydroxy-1-phenyl-2,3,4,5-tetrahydro-1H-3-benzazepine hydrobromide in 200 ml of methanol saturated with hydrogen chloride gas was heated at reflux for 60 hours. The solvent was stripped off and the residue was triturated with ethyl acetate, then recrystallized from methanol-ethyl acetate to give 6-carbomethoxy-7,8-dihydroxy-1-phenyl-2,3,4,5-tetrahydro-1H-3-benzazepine hydrochloride, m.p. 216°–219° (dec.).

EXAMPLE 6

(A). A mixture of 7.8 g (0.0225 mole) of 6-bromo-7,8-methylenedioxy-1-phenyl-2,3,4,5-tetrahydro-1H-3-benzazepine in toluene was added to a mixture of 2.2 ml (6.07 mole) of butyl lithium diluted with 100 ml of ethyl ether at −78°. Then, 10 ml of N-methylformanilide was added. After stirring for 1 hour at −78°, the cooling bath was removed and 100 ml of 10% hydrochloric acid was added. After stirring for 15 minutes, the layers were separated. The ether layer was dried and evaporated. The residue was dissolved in ethyl acetate then extracted by aqueous sodium bisulfite. The aqueous layer was removed, washed with ether and made basic with solid carbonate. After extraction with ethyl ether the extracts were evaporated. The residue was heated in 6 N hydrochloric acid for 1 hour. The solution was made basic and the product extracted into chloroform. After purification over silica with 5% methanol-chloroform, 6-formyl-7,8-methylenedioxy-1-phenyl-2,3,4,5-tetrahydro-1H-3-benzazepine was obtained as an oil.

This product (2 g, 0.007 mole) was dissolved in 200 ml of methylene chloride, cooled to −15° and 2 ml of boron tribromide added. After reaction as described above, the desired 6-formyl-7,8-dihydroxy-1-phenyl-2,3,4,5-tetrahydro-1H-3-benzazepine hydrobromide was obtained, m.p. 280°–286° (dec. 286°–294°).

The 6-formyl-7,8-dimethoxy product was reacted with methyl lithium then hydrochloric acid to give the 6-α-hydroxyethyl and 6-α-chloroethyl-7,8-dimethoxy-1-phenyl-2,3,4,5-tetrahydro-1H-3-benzazepine derivatives successively.

The reaction described above was run on the 7,8-dimethoxy congener to give 6-formyl-7,8-dimethoxy-1-phenyl-2,3,4,5-tetrahydro-1H-3-benzazepine hydrochloride, m.p. 209°-210°. Boron tribromide treatment gave the diol in 66% yield as the hydrochloride (blackens 290°, dec. 318°-323°).

(B). 6-Bromo-3-formyl-7,8-dimethoxy-1-phenyl-2,3,4,5-tetrahydro-1H-3-benzazepine (82.6 g, 0.212 m) was dissolved in 1500 ml of toluene and added to a mixture of 0.678 m of n-butyl lithium, 250 ml of toluene and 250 ml of ether at −78°. After addition, the mixture was stirred for 10 minutes. N-Methylformanilide (86 g, 0.636 m) was added to the mixture followed by stirring at −78° for 1 hour. The cooling bath was removed and 500 ml of 10% hydrochloric acid and 250 ml of water were added to give the 6-formyl derivative as the hydrochloride salt, m.p. 209°-210°, after standing overnight.

EXAMPLE 7

6-Carboxy-7,8-dimethoxy-1-phenyl-3-trifluoroacetyl-2,3,4,5-tetrahydro-1H-3-benzazepine (prepared by reaction of trifluoroacetic anhydride with the corresponding secondary amine) m.p. 118.5°-121° C., 6.0 g, 0.016 mole in 100 ml of dry methylene chloride was reacted with 1.6 ml of thionyl chloride. The mixture was heated at reflux for 4 hours then stripped to give the 6-acid chloride as an oil.

The oil was stirred in 100 ml of conc. ammonia over the weekend. The slurry was taken up in methylene chloride ethyl acetate. The dried organic layers were combined, dried and stripped and the remaining product was washed with ethyl acetate to give the desired 6-carbamyl-7,8-dimethoxy-1-phenyl-2,3,4,5-tetrahydro-1H-3-benzazepine, m.p. 178.5°-180°. The dihydroxy congener is obtained by boron tribromide-methylene dichloride treatment, m.p. 267° (dec.).

Reaction as above with methylamine or dimethylamine gives the methylated derivatives of these compounds.

EXAMPLE 8

Using the general process of Examples 7, 7,8-dimethoxy-1-phenyl-3-trifluoroacetyl-2,3,4,5-tetrahydro-1H-3-benzazepine-6-acid chloride was obtained as a yellow oil. This material was converted to the 2-amino end product via sodium azide, a Curtius rearrangement then alkali treatment to give a product obtained as a yellow oil. This material was treated with boron tribromide to give 6-amino-7,8-dihydroxy-1-phenyl-2,3,4,5-tetrahydro-1H-3-benzazepine dihydrobromide, m.p. 220°(dec.) a dopaminergic agent.

EXAMPLE 9

A mixture of 9.5 g (0.021 mole) of 6-carbomethoxy-7,8-dimethoxy-1-phenyl-3-trifluoroacetyl-2,3,4,5-tetrahydro-1H-3-benzazepine in dry toluene was reacted with 39 ml of methyl lithium in 100 ml of dry ethyl ether at 0° for one hour after dropwise addition. An additional excess of 10 ml of methyl lithium in ether was added and the reaction mixture was allowed to react for another hour.

The reaction was worked up by adding an excess of 10% hydrochloric acid and allowing it to stand at room temperature overnight. The non-organic layer and precipitate were collected, made basic with alkali and extracted by ethyl acetate. The toluene reaction mixture was taken through the salt isolation. The combined product as the base was dissolved in ether, made acid with ethereal hydrogen chloride to form the hydrochloride salt and purified by recrystallization from methanol-ethyl acetate to give 6-acetyl-7,8-dimethoxy-1-phenyl-2,3,4,5-tetrahydro-1H-3-benzazepine hydrochloride, m.p. 235°-236°.

The reaction was repeated on 22 g of the benzyl ester to give the free base in 60% yield as a yellow oil purified over a silica column using methanol-chloroform.

EXAMPLE 10

A mixture of 1.5 g of 6-formyl-7,8-dihydroxy-1-phenyl-2,3,4,5-tetrahydro-1H-3-benzazepine hydrobromide in 50 ml of methylene chloride was treated with trifluoroacetic anhydride. The product isolated was 6-formyl-8-trifluoroacetoxy-N-trifluoroacetyl-7-hydroxy-1-phenyl-2,3,4,5-tetrahydro-1H-3-benzazepine, infrared spectrum shows 3 keto absorption bands at

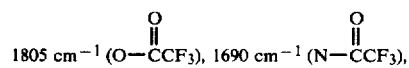

and 1650 cm⁻¹ (CH=O——HO).

EXAMPLE 11

A mixture of 4 g (0.1 mole) of 6-carboxy-7,8-dihydroxy-3-trifluoroacetyl-1-phenyl-2,3,4,5-tetrahydro-1H-3-benzazepine, prepared by boron tribromide treatment of the 7,8-dimethoxy congener, in 50 ml of dry dimethylformamide is reacted with 0.35 ml of benzyl chloride and 8.4 g of potassium carbonate at 160°-175°. The mixture was poured onto ice and taken through ether to give 93% of the desired dibenzyl ether.

This material, 6.2 g, was reacted with methyl lithium in ethyl ether at 0° as described above to give 6-acetyl-7,8-dibenzyloxy-1-phenyl-2,3,4,5-tetrahydro-1H-3-benzazepine, m.p. 229°-233°.

The dibenzyloxy compound, 2.4 g, in 100 ml of ethyl acetate, 10 ml of water and 1 ml of 10% hydrochloric acid with 200 mg of 10% palladium/charcoal was hydrogenated at 60° for two hours. The mixture was filtered. The filtrate is stripped. The residue was taken up in methanol. Ether was added to the cloud point to crystallize out the desired 6-acetyl-7,8-dihydroxy-1-phenyl-2,3,4,5-tetrahydro-1H-3-benzazepine hydrochloride, m.p. 251°-253°.

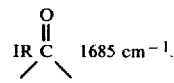

EXAMPLE 12

A mixture of 10 g (0.0255 mole) of 6-bromo-7,8-dimethoxy-1-(p-methoxyphenyl)-2,3,4,5-tetrahydro-1H-3-benzazepine and 42 ml of n-butyl lithium was reacted to give the 6-lithium derivative which is reacted with dry ice in excess as described above to give 6-carboxy-7,8-dimethoxy-1-(p-methoxyphenyl)-2,3,4,5-tetrahydro-1H-3-benzazepine hydrochloride, m.p. 242°-245° (dec.).

The trimethoxy product was treated with boron tribromide in methylene chloride to give the trihydroxy hydrobromide (4.5 g) which contained a small amount of the 6-carbomethoxy ester as by-product. This material (3.5 g) was esterified with 300 ml of methanol-hydrogen chloride by heating at reflux for 64 hours. The product was 6-carbomethoxy-7,8-dihydroxy-1-(p-hydroxyphenyl)-2,3,4,5-tetrahydro-1H-3-benzazepine hydrochloride, m.p. 226°–229°.

EXAMPLE 13

6-Bromo-3-formyl-7,8-dimethoxy-1-(p-methoxyphenyl)-2,3,4,5-tetrahydro-1H-3-benzazepine (15.4 g from N-formylation of the starting material from Example 12 using methylformate) was reacted with 53 ml of n-butyl lithium in 400 ml of toluene—300 ml of ether at −78° then with N-methylformanilide as described to give 6-formyl-7,8-dimethoxy-1-(p-methoxyphenyl)-2,3,4,5-tetrahydro-1H-3-benzazepine hydrochloride, m.p. 131°–136°.

EXAMPLE 14

A 4.2 g sample of 3-benzyl-6-carbomethoxy-7,8-dihydroxy-1-phenyl-2,3,4,5-tetrahydro-1H-3-benzazepine (prepared from the 3-unsubstituted benzazepine by reaction with benzyl bromide in the presence of potassium carbonate) is dissolved in 50 ml of acetic anhydride and the solution is heated on a steam bath for one hour. The reaction mixture is cooled, ice-water is added and the solution is evaporated to dryness. The residue is triturated with ethyl acetate, the solution washed with water, dried and the solvent removed in vacuo to leave an oil. The latter is dissolved in ether and ethereal hydrogen chloride is added to precipitate 3-benzyl-6-carbomethoxy-7,8-diacetoxy-1-phenyl-2,3,4,5-tetrahydro-1H-3-benzazepine hydrochloride.

The diacetoxy compound prepared above, 3.5 g is dissolved in 100 ml of ethanol and 1 g of 10% palladium-on-carbon is added. The mixture is hydrogenated in a Parr apparatus at 50° under 50 psi of hydrogen for one hour. The reaction mixture is filtered and the filtrate is evaporated to give 6-carbomethoxy-7,8-diacetoxy-1-phenyl-2,3,4,5-tetrahydro-1H-3-benzazepine hydrochloride.

Alternatively 6-carbomethoxy-7,8-dihydroxy-1-phenyl-2,3,4,5-tetrahydro-1H-3-benzazepine hydrobromide (10 g) is dissolved in trifluoroacetic acid and reacted with a stoichiometric amount of acetyl chloride at room temperature. The next day the reaction mixture is evaporated and the residue recrystallized to give the desired diacetoxy derivative.

Substituting other alkanoyl anhydrides or chlorides gives various 7,8-alkanoyl derivatives.

EXAMPLE 15

A solution of 3.7 g of 6-carbomethoxy-7,8-dimethoxy-1-phenyl-2,3,4,5-tetrahydro-1H-3-benzazepine in 15 ml of formic acid and 10 ml of formaldehyde is refluxed for 18 hours. The reaction mixture is evaporated to dryness, 20 ml of 6N hydrochloric acid is added and the solution is again evaporated to dryness to give a liquid. The latter is treated with 20 ml of 10% sodium hydroxide solution and the mixture is extracted with ether. The dried extract is evaporated to give 6-carbomethoxy-7,8-dimethoxy-3-methyl-1-phenyl-2,3,4,5-tetrahydro-1H-3-benzazepine.

EXAMPLE 16

A 4.2 g sample of 6-carbomethoxy-7,8-dihydroxy-1-phenyl-2,3,4,5-tetrahydro-1H-3-benzazepine is slurried in 25 ml of acetone and 0.7 g (0.016 mol, 10% excess) of ethylene oxide is added. The mixture is placed in a pressure bottle and stirred at ambient temperature for about 40 hours. The reaction mixture is then heated to 60°–80° for 30 minutes, cooled and filtered. Concentration of the filtrate gives a solid which is taken up in ethyl acetate and reprecipitated with ether. The solid thus obtained is dissolved in ethanol and treated with ethereal hydrogen chloride to give 6-carbomethoxy-7,8-dihydroxy-3-(2-hydroxyethyl)-1-phenyl-2,3,4,5-tetrahydro-1H-3-benzazepine hydrochloride.

EXAMPLE 17

Using N-alkylation or N-acylation procedures described above but using 6-carbomethoxy-7,8-dimethoxy-1-phenyl-2,3,4,5-tetrahydro-1H-3-benzazepine as a model compound the N-allyl, N-butyl, N-amyl, N-propargyl, N-phenacyl or N-2,2-dimethylallyl derivatives are prepared. Hydrolysis of the methoxy groups as described gives the more active 6-carbomethoxy-7,8-dihydroxy compounds.

EXAMPLE 18

Using the chemical processes of Examples 1–5 and the following starting materials:
6-bromo-1-(p-chloro-m-methoxyphenyl)-7,8-dimethoxy-2,3,4,5-tetrahydro-1H-3-benzazepine
6-bromo-1-(p-methylthiophenyl)-7,8-dimethoxy-2,3,4,5-tetrahydro-1H-3-benzazepine
6-bromo-1-(o-methylphenyl)-7,8-dimethoxy-2,3,4,5-tetrahydro-1H-3-benzazepine
6-bromo-1-(m-methoxyphenyl)-7,8-dimethoxy-2,3,4,5-tetrahydro-1H-3-benzazepine
6-bromo-1-(p-ethoxyphenyl)-7,8-dimethoxy-2,3,4,5-tetrahydro-1H-3-benzazepine
gives the corresponding 6-carboxy and 6-carbomethoxy compounds of this invention.

EXAMPLE 19

A mixture of 7.5 g of 7,8-dimethoxy-6-α-hydroxypropyl-1-phenyl-2,3,4,5-tetrahydro-1H-3-benzazepine in 500 ml of ethylformate was heated at reflux for 5 hours then worked up using medium pressure liquid chromatography to give the N-formyl derivative.

This material (4.9 g) in 150 ml of chloroform and 50 ml of concentrated hydrochloric acid was heated at reflux for 2 hours. A small amount of aldehyde by-product was removed by bisulfite extraction to give the 6-α-chloropropyl compound.

This material (3.6 g) in dry dimethylsulfoxide was added dropwise to a solution of 1.07 (0.028 mole) of sodium borohydride in dry dimethyl sulfoxide. After stirring at room temperature the mixture was heated on the steam bath for several hours then poured into water. The product was taken into ethyl ether-ethyl acetate and purified by chromatography using methanol-chloroform to give 3-formyl-7,8-dimethoxy-6-propyl-1-phenyl-2,3,4,5-tetrahydro-1H-3-benzazepine.

This material (1.9 g, 0.0054 mole) in 50 ml of ethanol and 10 ml of 40% sodium hydroxide was heated at reflux for 2 hours. After stripping, the residue was taken up in methylene chloride-water. The combined organic layers were dried and evaporated to give the 7,8-dimethoxy compound which (1 g) was reacted with 1 ml of boron tribromide in dry methylene chloride for 3 hours. After stripping and cooling the residue was treated with methanol. The methanol was taken off and the residue dissolved in hot water (20 ml). Evaporation and cooling gave the dopaminergic agent 7,8-dihydroxy-6-n-propyl-1-phenyl-2,3,4,5-tetrahydro-1H-3-benzazepine hydrobromide, m.p. 226°–229° (dec.).

Using methods described herein the following dopaminergically active compounds are prepared:

7,8-Dihydroxy-6-methyl-1-phenyl-2,3,4,5-tetrahydro-1H-3-benzazepine hydrobromide hydrate, m.p. 160°–163°

7,8-Dihydroxy-3-methyl-6-propyl-1-phenyl-2,3,4,5-tetrahydro-1H-3-benzazepine hydrobromide hydrate, m.p. 211°–213°

7,8-Dihydroxy-3,6-dimethyl-1-phenyl-2,3,4,5-tetrahydro-1H-3-benzazepine hydrobromide hydrate, m.p. 168°–176°

7,8-Dihydroxy-6-ethyl-3-methyl-1-phenyl-2,3,4,5-tetrahydro-1H-3-benzazepine hydrobromide hydrate, m.p. 160° (dec.).

EXAMPLE 20

| Ingredients | Mg. per Capsule |
| --- | --- |
| 6-Carbomethoxy-7,8-dihydroxy-3-methyl-1-phenyl-2,3,4,5-tetrahydro-1H-3-benzazepine (as an acid addition salt) | 150 (free base) |
| Magnesium stearate | 2 |
| Lactose | 200 |

The above ingredients are thoroughly mixed and placed into hard gelatin capsules. Such capsules are administered orally to subjects in need of treatment from 1–5 times daily to induce dopaminergic activity.

EXAMPLE 21

| Ingredients | Mg. per Tablet |
| --- | --- |
| 6-Carbomethoxy-7,8-dihydroxy-1-(p-hydroxyphenyl)-2,3,4,5-tetrahydro-1H-3-benzazepine hydrochloride | 200 (free base) |
| Corn starch | 30 |
| Polyvinyl pyrrolidone | 12 |
| Corn starch | 16 |
| Magnesium stearate | 3 |

The first two ingredients are thoroughly mixed and granulated. The granules obtained are dried, mixed with the remaining corn starch and magnesium stearate, and compressed into tablets.

The capsules or tablets thusly prepared are administered orally to an animal or human requiring stimulation of dopamine receptors at either central or peripheral sites within the dose ranges set forth hereinabove. Similarly other biologically active compounds of Formula I and the illustrative examples can be formulated in the same manner to give pharmaceutical compositions useful in the methods of this invention based on the chemical characteristics and relative biological activity using the test methods outlined.

What is claimed is:

1. A chemical compound of the structural formula:

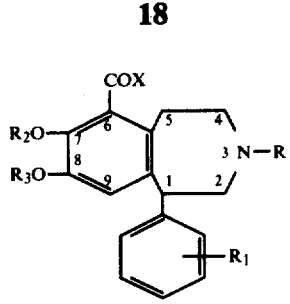

in which:

R is hydrogen, benzyl, phenethyl, lower alkanoyl of from 1–5 carbons, lower alkyl of from 1–5 carbons, lower alkenyl of 3–5 carbons, hydroxyethyl, propargyl or phenacyl;

$R_1$ is hydrogen or one or two substituents from the group of trifluoromethyl, halo, methyl, methoxy, acetoxy, methylthio or hydroxy;

$R_2$ and $R_3$ are respectively hydrogen, benzyl, lower alkyl of 1–5 carbon atoms, lower alkanoyl of 2–5 carbon atoms, or when taken together, methylene; and X is hydroxy, amino, lower alkyl of 1–5 carbons or lower alkoxy of 1–5 carbons; together with pharmaceutically acceptable acid addition or alkali metal salts thereof.

2. The compound of claim 1 in which:
X is hydroxy or lower alkoxy of 1–5 carbons;
R is hydrogen or methyl;
$R_2$ and $R_3$ are hydrogen; and
$R_1$ is hydrogen or p-hydroxy.

3. The compound of claim 1 in which X is hydroxy or lower alkoxy of 1–5 carbons.

4. The compound of claim 2 in which X is methoxy.

5. The compound of claim 2 in which X is hydroxy.

6. The compound of claim 1 in which $R_2$ and $R_3$ are methyl.

7. The compound of claim 2 in which X is methoxy, R is methyl and $R_1$, $R_2$ and $R_3$ are hydrogen.

8. The compound of claim 7 in which the compound is the hydrochloride salt.

9. The compound of claim 2 in which X is methoxy, R is methyl or hydrogen, $R_2$ and $R_3$ are hydrogen and $R_1$ is p-hydroxy.

10. The compound of claim 9 in which the compound is the hydrochloride salt.

11. The compound of claim 9 in which X is methoxy, R, $R_2$ and $R_3$ are hydrogen and $R_1$ is p-hydroxy together with its pharmaceutically acceptable acid addition salts.

12. A pharmaceutical composition consisting essentially of a nontoxic dopaminergically quantity of a compound of claim 1 combined with a pharmaceutical carrier.

13. A pharmaceutical composition consisting essentially of a nontoxic dopaminergic quantity of a compound of claim 2 combined with a pharmaceutical carrier.

14. The method of producing dopaminergic activity in a subject in need thereof comprising the step of administering orally or parenterally to said subjects a nontoxic amount of a compound of claim 1 which is effective therefor.

15. A chemical compound of the structural formula:

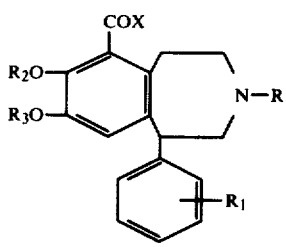

in which:

R is hydrogen, benzyl, phenethyl, lower alkanoyl of from 1-5 carbons, lower alkyl of from 1-5 carbons, lower alkenyl of 3-5 carbons, hydroxyethyl, propargyl or phenacyl;

$R_1$ is hydrogen or one or two substituents from the group of trifluoromethyl, halo, methyl, methoxy, acetoxy, methylthio or hydroxy;

$R_2$ and $R_3$ are respectively hydrogen, benzyl, lower alkyl of 1-5 carbon atoms, lower alkanoyl of 2-5 carbon atoms, or when taken together, methylene; and X is hydrogen, chloro or bromo; together with acid addition salts thereof suitable for chemical intermediate use.

* * * * *